(12) United States Patent
Wall

(10) Patent No.: US 12,245,998 B2
(45) Date of Patent: Mar. 11, 2025

(54) N-ACETYLCYSTEINE AMIDE (NACA) AND (2R,2R')-3,3' DISULFANEDIYL BIS(2-ACETAMIDOPROPANAMIDE) (diNACA) FOR THE PREVENTION AND TREATMENT OF RADIATION PNEUMONITIS AND TREATMENT OF PULMONARY FUNCTION IN CYSTIC FIBROSIS

(71) Applicant: NACUITY PHARMACEUTICALS, INC., Fort Worth, TX (US)

(72) Inventor: G. Michael Wall, Fort Worth, TX (US)

(73) Assignee: Nacuity Pharmaceuticals, Inc., Fort Worth, TX (US)

( * ) Notice: Subject to any disclaimer, the term of this patent is extended or adjusted under 35 U.S.C. 154(b) by 841 days.

(21) Appl. No.: 17/421,318

(22) PCT Filed: Jan. 9, 2020

(86) PCT No.: PCT/US2020/012968
§ 371 (c)(1),
(2) Date: Jul. 7, 2021

(87) PCT Pub. No.: WO2020/146660
PCT Pub. Date: Jul. 16, 2020

(65) Prior Publication Data
US 2022/0062203 A1    Mar. 3, 2022

Related U.S. Application Data

(60) Provisional application No. 62/791,442, filed on Jan. 11, 2019.

(51) Int. Cl.
*A61K 31/16* (2006.01)
*A61K 45/06* (2006.01)
*A61P 11/12* (2006.01)

(52) U.S. Cl.
CPC .............. *A61K 31/16* (2013.01); *A61K 45/06* (2013.01); *A61P 11/12* (2018.01)

(58) Field of Classification Search
None
See application file for complete search history.

(56) References Cited

U.S. PATENT DOCUMENTS 3,340,147 A     9/1967 Martin
5,874,468 A     2/1999 Atlas et al.
(Continued)

FOREIGN PATENT DOCUMENTS

CA     2670468 A1    5/2008
CA     3079196       3/2019
(Continued)

OTHER PUBLICATIONS

Komeina, et al., "Antioxidants slow photoreceptor cell death in mouse models of retinitis pigmentosa." J Cell Physiol. (2007), 213(3):809-15.
(Continued)

*Primary Examiner* — Jeffrey S Lundgren
*Assistant Examiner* — Anthony Joseph Seitz
(74) *Attorney, Agent, or Firm* — Edwin S. Flores; Daniel J. Chalker; Chalker Flores, LLP

(57) ABSTRACT

The present invention includes a method for the use of N-acetylcysteine amide (NACA) or (2R,2R')-3,3'-disulfanediyl bis(2-acetamidopropanamide) (diNACA) for prevention and treatment of radiation pneumonitis and treatment of pulmonary function in Cystic Fibrosis (CF), chronic obstructive pulmonary disease (COPD), or bronchitis in a human that comprises administering to the human a therapeutically effective amount of NACA or diNACA sufficient to treat, reduce the symptoms, or prevent radiation pneumonitis and treatment of pulmonary function in Cystic (Continued)

Fibrosis (CF), chronic obstructive pulmonary disease (COPD), bronchitis, or respiratory disorder due to oxidative stress, and diNACA for the reduction of mucus viscosity and/or elasticity.

15 Claims, 4 Drawing Sheets

(56) References Cited

U.S. PATENT DOCUMENTS

| | | | |
|---|---|---|---|
| 6,420,429 | B1 | 7/2002 | Atlas et al. |
| 8,258,173 | B2 | 9/2012 | Anderson et al. |
| 8,354,449 | B2 | 1/2013 | Goldstein |
| 8,937,099 | B2 | 1/2015 | Goldstein |
| 8,993,627 | B2 | 3/2015 | Goldstein |
| 9,216,162 | B2 | 12/2015 | Goldstein |
| 9,763,902 | B2 | 9/2017 | Warner et al. |
| 9,889,103 | B2 | 2/2018 | Warner et al. |
| 10,869,846 | B2 | 12/2020 | Goldstein |
| 11,052,018 | B2 | 7/2021 | Molnar |
| 11,092,017 | B2 | 8/2021 | Propheter-Hinckley et al. |
| 2021/0228509 | A1* | 7/2021 | Wall ............... A61K 9/0019 |

FOREIGN PATENT DOCUMENTS

| | | | |
|---|---|---|---|
| CA | 3078680 A1 | 5/2019 | |
| EP | 1975621 L | 10/2008 | |
| GB | 1114369 A | 5/1968 | |
| JP | 202023549 | 5/1968 | |
| JP | 2005-350405 | 12/2005 | |
| JP | 2008-538586 | 10/2008 | |
| JP | 2013-533234 | 8/2013 | |
| WO | 2003016527 | 2/2003 | |
| WO | 2004012652 A2 | 2/2004 | |
| WO | 2004028536 A1 | 4/2004 | |
| WO | WO-2006116353 A2 * | 11/2006 | ............. A61K 31/16 |
| WO | WO-2010048716 A1 * | 5/2010 | ........... A61K 31/196 |
| WO | 2011044230 A2 | 4/2011 | |
| WO | 2013138744 A1 | 9/2013 | |
| WO | 2013163545 A1 | 10/2013 | |
| WO | 2014100361 A1 | 6/2014 | |
| WO | 2015148880 A1 | 10/2015 | |
| WO | 2016073829 A2 | 5/2016 | |
| WO | 2016073931 A1 | 5/2016 | |
| WO | 2017161318 A1 | 9/2017 | |
| WO | 2019060623 A1 | 3/2019 | |
| WO | 2019060634 A1 | 3/2019 | |
| WO | 2019060704 A1 | 3/2019 | |
| WO | 2019094383 A1 | 5/2019 | |
| WO | 2019097434 A1 | 5/2019 | |
| WO | 2019103915 A1 | 5/2019 | |
| WO | 2020146660 A1 | 7/2020 | |
| WO | 2020146666 A1 | 7/2020 | |
| WO | 2020146674 A1 | 7/2020 | |
| WO | 2014025792 A1 | 2/2024 | |

OTHER PUBLICATIONS

Komeina, et al., "Blockade of neuronal nitric oxide synthase reduces cone cell death in a model of retinitis pigmentosa." Free Radic Biol Med, (2008), 45(6):905-12.

Kusmierek, et al., Ultraviolet derivatization of low-molecular-mass thiols for high performance liquid chromatography and capillary electrophoresis analysis, J Chrom B, 879 (2011) 1290-1307.

Grinberg, et al., "N-acetylcysteine amide, a novel cell-permeating thiol, restores cellular glutathione and protects human red blood cells from oxidative stress," Free Radical Biol Med. (2005);38(1):136-145.

Lee, et al., "N-Acetylcysteine Promotes Long-Term Survival of Cones in a Model of Retinitis Pigmentosa," J Cell Physiol (2011), 226:1843-1849, published online Nov. 10, 2010.

Li, et al, "A Convenient Synthesis of Amino Acid Methyl Esters", Molecules (2008), 13:1111-1119.

Liu, et al., "A rabbit model to study biochemical damage to the lens after vitrectomy: effects of N-acetylcysteine." Exp Eye Res. 2009;88(6):1165-70.

Lu, et al., "Effects of Different Types of Oxidative Stress in RPE Cells," J Cell Phys (2006), 206(1):119-125.

Maddirala, et al. "Prevention and reversal of selenite-induced cataracts by N-acetylcysteine amide in Wistar rats" BMC Ophthalmology (2017) 17:54.

Maeda, et al., "Important Role of the 3-Mercaptopropionamide Moiety in Glutathione: Promoting Effect on Decomposition of the Adduct of Glutathione with the Oxoammonium Ion of Tempo", J Organic Chem (2005). 70:8338-8343.

Martin, Tellis, "Amides of N-Acylcysteines as Mucolytic Agents", J Med Chem (1967), 10:1172-1176.

Martinez-Fernandez De La Camara, et al., Altered Antioxidant-Oxidant Status in Aqueous Humor and Peripheral Blood of Patents with Retinitis Pigmentosa, PLoS One (2013), 8(9):E74223.

McMenamim, et al., Simultaneous analysis of multiple aminothiols in human plasma by high performance liquid chromatography with fluorescence detection, J Chrom B, 877 (2009) 3274-3281.

Minozzi et al., "An Insight into the Radical Thiol/Yne Coupling: The Emergence of Arylalkyne-tagged Suggars for te Direct Photoinduced Glycosylation of Cysteine Containing Peptides", J. Org. Chem, 2011, 76, 450-459.

Miller, WF. "Aerosol therapy in acute and chronic respiratory disease." Arch Intern Med 1973;131:148-155.

Monostori, et al., Determination of glutathione and glutathione disulfide in biological samples: an in-depth review. J Chrom B, 877 (2009) 3331-3346.

Moore, et al., A new LC-MS/MS method for the clinical determination of reduced and oxidized glutathione from whole blood. J Chrom B, 929 (2013) 51-55.

Nakagami, et al. "A novel Nrf2 activator from microbial transformation inhibits radiation-induced dermatitis in mice," Journal of Radiation Research, vol. 57, No. 5, 2016, pp. 567-571.

Nash, et al., "Nebulized and oral thiol derivatives for pulmonary disease in cystic fibrosis." Cochrane Database Syst Rev 2009;(1):CD007168.

New, et al., Evaluation of BEH C18, BEH HILIC, and HSS T3 (C18) Column Chemistries for the UPLC-MS-MS Analysis of Glutathione, Glutathione Disulfide, and Ophthalmic Acid in Mouse Liver and Human Plasma. J Chrom Sci, 46 (2008) 209-214.

Niemeyer, Selective Rod-and Cone-ERG Responses on Retinal Degenerations, Digital Journal of Ophthalmology, 1998, vol. 4, No. 10, 1998.

Nozal, et al., Determination of glutathione, cysteine, and N-acetylcysteine in rabbit eye tissues using high-performance liquid chromatography and post-column derivatization with 5,5'-dithiobis(2-nitrobenzoic acid). J Chrom A, 778 (1997) 347-353.

Park, et al.: "Targeted and Reversible Blood-Retinal Barrier Disruption via Focused Ultrasound and Microbubbles" PLoS One (2012), 7(8):e42754.

Poole, et al., "Mucolytic agents versus placebo for chronic bronchitis or chronic obstructive pulmonary disease." Cochrane Database Syst Rev 2015;(7):CD001287).

Reyes, et al., Neuronal glutathione content and antioxidant capacity can be normalized in situ by N-acetyl cysteine concentrations attained in human cerebrospinal fluid, Neurotherapeutics, 13 (2016) 217-225.

Riley, et al., "Glutathione in the aqueous humor of human and other species." Investigative ophthalmology & visual science, (1980), 9(1):94-96.

Rubin BK. "Aerosol Medications for Treatment of Mucus Clearance Disorders Respiratory care" 2015; 60(6): 825-832.

Šalamon, et al., "Medical and Dietary Uses of N-Acetylcysteine." Antioxidants 2019, 8, 111.

Schimel, et al., "N-Acetylcysteine Amide (NACA) Prevents Retinal Degeneration by Up-Regulating Reduced Glutathione Production and Reversing Lipid Peroxidation." The American Journal of Pathology, (2011), 178(5):2032-2043.

(56) References Cited

OTHER PUBLICATIONS

Sekhon, "Exploiting the Poer of Stereochemistry in Drugs . . . . ", Journal of Modern Medicinal Chemistry, 2013, 10-36.
Shen, et al., "Oxidative damage is a potential cause of cone cell death in retinitis pigmentosa." J Cell Physiol, (2005), 203(3):457-64.
Shen, et al., "Oxidative damage in age-related macular degeneration," Histology and Histopathology (2007), 22(12):1301-1308.
Shintani, et al., "Review and Update: Current treatment trends for Patients with Retinitis Pigmentosa," Optometry (2009), 80:384-401.
Supelco "Methanolic H2S04 (10./o v/v)" 1997, Sigma-Aldrich Co., 2 Pages.
Squellerio, et al., Direct glutathione quantification in human blood by LC-MS/MS: comparison with HPLC with electrochemical detection. J Pharm Biomed Anal, 71 (2012) 111-8.
Stey, et al., "The effect of oral N-acetylcysteine in chronic bronchitis: a quantitative systematic review." Eur Respir J. 2000; 16(2):253-62.
Suh, et al., Clinical assay of four thiol amino acid redox couples by LC-MS/MS: utility in thalassemia, J Chrom B, 877 (2009) 3418-3427.
Sunitha, et al., N-acetylcysteine amide: a derivative to fulfull the promises of N-acetylcysteine. Free Radic Res, 47 (2013) 357-367.
Tam, et al., "Nebulized and oral thiol derivatives for pulmonary disease in cystic fibrosis." Cochrane Database Syst Rev 2013;(7):CD007168.
Tarrant et al. "Mucoactive agents for adults with acute lung conditions: A systematic review." Heart & Lung (2019) 48(2):141-147.
Tobwala et al. "N-acetylcysteine Amide (NACA), a Novel GSH Prodrug: Its Metabolism and Implications in Health", Labrou, 2013, Capter VI. ISBN:978-1-62417-460-5.
Tse, et al., "High-dose N-acetylcysteinine in stable COPD: the 1-year, double-blind, randomized, placebo-controlled HIACE study." Chest, (2013). 144(1):106-118.
Tuson, et al., "Overexpression of CERKL, a gene responsible for retinitis pigmentosa in humans, protects cells from apoptosis induced by oxidative stress." Mol Vis. (2009), 15:168-80.
United States Patent & Trademark Office (ISA) International Search Report and Written Opinion PCT/US2015/059589 Dated Feb. 2, 2016, 10 pg.
Usui, et al., "Overexpression of SOD in retina: Need for increase in H202-detoxifying enzyme in same cellular compartment," Free Radical Biology and Medicine (2011 ), 51(7):1347-1354.
Usui, et al., "Increased expression of catalase and superoxide dismutase 2 reduces cone cell death in retinitis pigmentosa." Mol Ther J Am Soc Gene Ther. (2009), 17(5):778-86.
Usui, et al., "NADPH oxidase plays a central role in cone cell death in retinitis pigmentosa." J Neurochem. (2009), 110(3):1028-37.
Wang, et al., "Relationship of protein-glutathione mixed disulfide and thioltransferase in H2O2-induced cataract in cultured pig lens." Exp Eye Res. May 1997;64(5):693-700.
Wang, et al., "Hyperoxia-induced lens damage in rabbit: protective effects of N-acetylcysteine." Mol Vis. 2009;15:2945-52.
Watanabe, et al., "Skin-whitening and skin-condition-improving effects of topical oxidized glutathione: a double-blind and placebo-controlled clinical trial." Clin Cosmetic Inv Dermatol. 2014;7:267-274.
Weng, Bioanalytical liquid chromatography tandem mass spectrometry methods on underivatized silica columns with aqueous/organic mobile phases. J Chrom B, 796 (2003) 209-224.
Wu, et al., "Effects of N-acetylcysteine amide (NACA, a thiol antioxidant on radiation-induced cytotoxicity in Chenese hamster ovary cells," Life Sciences (2008), 82:1122-1130.
Wu, et al., Separation and quantification of N-acetyl-L-cysteine and N-acetyl cysteine-amide by HPLC with fluorescence detection. Biomed Chromatogr, 20 (2006) 415-422.
Yu, et al., "Intraretinal oxygen levels before and after photoreceptor loss in the RCS rat." Invest Ophthalmol Vis Sci, (2000), 41(12):3999-4006.
Zhang, et al., "Effects of N-acetylcysteine and glutathione ethyl ester drops on streptozotocin-induced diabetic cataract in rats." Mol Vis. 2008;14:862-70.
Adil, et al. "N-acetylcysteine in dermatology" Indian Journal of Dermatology, Feb. 2018.
Demirel, et al. "The preventive effect of N-acetylcysteine on radiation-induced dermatitis in a rat model" Journal of Buon, 15:577-582, 2010.
Hong, et al. "Effect of High-Dose Intravenous N-acetylcysteine on the Concentration of Plasma Sulfur-Containing Amino Acids", The Korean Journal of Internal Medicine: 20:217-223, 2005.
Hsu, et al. "Feasibility of corneal drug delivery of cysteamine using vitamin E modified silicone hydrogel contact lenses" European Journal of Pharn1aceutics and Biopharn1aceutics 85 (2013) 531-540.
Kunisada, et al. "CXCL1 Inhibition Regulates UVB-Induced Skin Inflammation and Tumorigenesis in Xpa-Deficient Mice" Journal of Investigative Dermatology (2017), 137, 1975-1983.
Levine, R.L., "Carbonyl modified proteins in cellular regulation, aging, and disease" Free Radic Biol Med, 2002. 32(9): p. 790-6.
Offen, et al. "A low molecular weight copper chelator crosses the blood-brain barrier and attenuates experimental autoimmune encephalomyelitis" Journal of Neurochemistry, 2004, 89, 1241-1251.
Reagan-Shaw, et al. "Dose translation from animal to human studies revised" The FASEB Journal, Mar. 2007, vol. 22, (659-661).
Shams, et al. "Treatment of corneal cystine crystal accumulation in patients with cystinosis" Clinical Opthamalogy, Oct. 10, 2014, 2077-2078.
Sunitha, et al. "N-Acetylcysteine amide: a derivative to fulfill the promises of N-Aceylcysteine" Free Radical Resarch, May 2013, 47(5), 357-367.
Tsai, et al. "Topical TV-Acetylcysteine Accelerates Wound Healing in Vitro and in Vivo via the PKC/Stat3 Pathway" Int. J. Mol. Sci., 2014, 15, 7563-7578.
University of Sao Paulo, et al. "N-Acetyl Cysteine for Cystinosis Patients", ClinicalTrials.gov [online], identifier: NCT01614431, Last update posted: Jun. 20, 2012, htps://clinicaltrials.gov/ct2/show/NCT01614431, [retrieved online Jul. 9, 2021].
Vaisbich, et al. "Oxidative Stress in Cystinosis Patients" Nephron Extra, 2011; 1:73-77, publishes online Sep. 19, 2011.

* cited by examiner

N-ACETYLCYSTEINE AMIDE (NACA) AND (2R,2R')-3,3' DISULFANEDIYL BIS(2-ACETAMIDOPROPANAMIDE) (diNACA) FOR THE PREVENTION AND TREATMENT OF RADIATION PNEUMONITIS AND TREATMENT OF PULMONARY FUNCTION IN CYSTIC FIBROSIS

CROSS-REFERENCE TO RELATED APPLICATIONS

This application is the National Stage of International Application No. PCT/US2020/012968, filed on Jan. 9, 2020, which claims priority to U.S. Provisional Patent Application Ser. No. 62/791,442, filed on Jan. 11, 2019. The contents of both applications are incorporated by reference herein in their entirety.

STATEMENT OF FEDERALLY FUNDED RESEARCH

None.

TECHNICAL FIELD OF THE INVENTION

The present invention relates in general to the use of N-acetylcysteine amide (NACA) or (2R,2R')-3,3'-disulfanediyl bis(2-acetamidopropanamide)(diNACA) for prevention and treatment of radiation pneumonitis and treatment of pulmonary function in Cystic Fibrosis, treatment of chronic obstructive pulmonary disease (COPD), prevention or treatment of bronchitis, and prevention and treatment of respiratory disorders due to oxidative stress, and diNACA as a mucolytic agent.

BACKGROUND OF THE INVENTION

Radiation pneumonitis is one of the most hazardous complications of concurrent chemoradiation for lung cancer and esophageal cancer. Since concurrent chemoradiotherapy began to demonstrate benefits for locally advanced lung cancer, radiotherapy has remained an important component of treatment. However, other than supportive care, there is no established treatment for radiation pneumonitis. (Han D W; Ji W; Lee J C; Song S Y; Choi C M. Efficacy of nebulized acetylcysteine for relieving symptoms and reducing usage of expectorants in patients with radiation pneumonitis. Thoracic Cancer 2018; 1-6. doi: 10.1111/1759-7714.12938) With treatment periods of approximately 12-24 weeks, oral N-acetylcysteine reduces the risk of exacerbations and improves symptoms in patients with chronic bronchitis compared with placebo, without increasing the risk of adverse effects. (Stey C; Steurer J; Bachmann S; Medici T C; Tramer M R. The effect of oral N-acetylcysteine in chronic bronchitis: a quantitative systematic review. Eur Respir J. 2000; 16(2):253-62.)

N-Acetylcysteine amide (NACA) was patented as a mucolytic agent in 1967 (U.S. Pat. No. 3,340,147) and found to exhibit greater mucolytic activity via liquefication of human sputa, but to the inventor's knowledge, never clinically investigated. The airway mucosa responds to acute infection and inflammation with mucus hypersecretion and secretion (phlegm) retention. With chronic exposure, there is mucous (goblet) cell and submucosal gland hyperplasia and hypertrophy. Products of inflammation (including neutrophil-derived deoxyribonucleic acid [DNA] and filamentous actin), dead cells, bacteria, and cell debris all contribute to sputum purulence. Mucus is usually cleared by ciliary movement, and sputum is cleared by cough. Mucoactive medications are intended to increase the ability to expectorate sputum or to decrease mucus hypersecretion, and these medications are classified based on their proposed method of action. (Rubin B K. Aerosol Medications for Treatment of Mucus Clearance Disorders Respiratory care 2015; 60(6): 825-832) Dornasealfa, hypertonic saline and NAC were ineffective for atelectasis/mucus plugging while intubated. More data are required to support using NAC, ambroxol and heparin during acute illness. (Tarrant et al. Mucoactive agents for adults with acute lung conditions: A systematic review. Heart & Lung 000 (2018)1-7.)

Glutathione, a tripeptide of cysteine, glycine, and glutamate, is a primary antioxidant in the body and plays important roles in maintaining intracellular thiol status and in detoxification. Although glutathione exists in both reduced (GSH) and oxidized (GSSG) states, the majority of its pool in the body is in the reduced form. GSH exerts antioxidant activity by acting as a free-radical scavenger during the reductive detoxification of hydrogen peroxide and lipid peroxide. In mammalian cells, GSH serves as an electron donor. During electron donation it is converted to GSSG by glutathione peroxidase, but it is reduced back to GSH by glutathione reductase in the presence of nicotinamide adenine dinucleotide phosphate. GSH has a variety of physiological effects.

SUMMARY OF THE INVENTION

In accordance with an embodiment, the present invention provides a method for the use of N-acetylcysteine amide (NACA) or (2R,2R')-3,3'-disulfanediyl bis(2-acetamidopropanamide) (diNACA) for prevention and treatment of radiation pneumonitis and treatment of pulmonary function in Cystic Fibrosis (CF), chronic obstructive pulmonary disease (COPD), bronchitis, or respiratory disorder due to oxidative stress, in an animal or human that comprises administering to the animal or human a therapeutically effective amount of NACA or diNACA. In one aspect, NACA or diNACA is provided in or with a pharmaceutically acceptable carrier. In another aspect, the NACA or diNACA is administered intraocularly, subretinally, intravitreally, orally, intravenously, intramuscularly, topically, sublingually, by inhalation, or rectally. In another aspect, the NACA or diNACA is administered in daily doses of about 0.5 to 150 mg/Kg. In another aspect, NACA is administered two or three times daily. In another aspect, NACA or diNACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytouene (BHT), lecithin, propyl gallate, α-tocopherol, citric acid, ethylenediamine tetraacetic acid (EDTA), sorbitol, tartaric acid, or phosphoric acid. In another aspect, the dose for administration is 100, 150, 150, 300, 333, 400, 500, 600, 700, 750, 800, 900, 1,000, 2,500, 5,000, 7,500, or 10,000 mg per dose. In another aspect, the does for administration is 0.1-0.25, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, the NACA or diNACA is delivered orally via a mini-tablet, capsule, tablet, effervescent, dual release, mixed release, sachet, powder, aerosol, spray or liquid. In another aspect, the NACA or diNACA is administered prophylactically to prevent age-related macular degeneration. In another aspect, the animal is a human. In another aspect, the diNACA reduces mucus viscosity, elasticity and/or cohesion.

In accordance with another embodiment, the present invention includes a method for the treatment of radiation pneumonitis and treatment of pulmonary function in Cystic Fibrosis (CF), chronic obstructive pulmonary disease (COPD), bronchitis or respiratory disorder due to oxidative stress, or reduction of mucus viscosity and/or elasticity comprising: identifying a human in need of treatment for radiation pneumonitis and treatment of pulmonary function in Cystic Fibrosis (CF), chronic obstructive pulmonary disease (COPD), bronchitis or respiratory disorder due to oxidative stress, or reduction of mucus viscosity and/or elasticity; and administering to the human a therapeutically effective amount of NACA or diNACA sufficient to treat radiation pneumonitis and treatment of pulmonary function in Cystic Fibrosis (CF), chronic obstructive pulmonary disease (COPD), or bronchitis. In one aspect, the NACA or diNACA is provided in or with a pharmaceutically acceptable carrier. In another aspect, the NACA or diNACA is administered intraocularly, subretinally, intravitreally, orally, intravenously, intramuscularly, topically, sublingually, by inhalation, or rectally. In another aspect, the NACA or diNACA is administered in daily doses of about 0.5 to 150 mg/Kg. In another aspect, NACA or diNACA is administered two or three times daily. In another aspect, NACA or diNACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytouene (BHT), lecithin, propyl gallate, α-tocopherol, citric acid, ethylenediamine tetraacetic acid (EDTA), sorbitol, tartaric acid, or phosphoric acid. In another aspect, the dose for administration is 100, 150, 150, 300, 333, 400, 500, 600, 700, 750, 800, 900, 1,000, 2,500, 5,000, 7,500, or 10,000 mg per dose. In another aspect, the does for administration is 0.1-0.25, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, the NACA or diNACA is delivered orally via a mini-tablet, capsule, tablet, effervescent, dual release, mixed release, sachet, powder, aerosol, spray or liquid. In another aspect, the NACA or diNACA is administered prophylactically to treat and/or prevent radiation pneumonitis and treatment of pulmonary function in Cystic Fibrosis (CF), chronic obstructive pulmonary disease (COPD), or bronchitis, or respiratory disorder due to oxidative stress, and diNACA as a mucolytic agent. In another aspect, the diNACA reduces mucus viscosity, elasticity and/or cohesion.

A method for prevention or treatment of radiation pneumonitis and treatment of pulmonary function in Cystic Fibrosis (CF), chronic obstructive pulmonary disease (COPD), or bronchitis in a human subject that comprises: administering to the human patient a therapeutically effective amount of NACA or diNACA sufficient to treat or prevent radiation pneumonitis and treatment of pulmonary function in Cystic Fibrosis (CF), chronic obstructive pulmonary disease (COPD), or bronchitis. In another aspect, the diNACA reduces mucus viscosity, elasticity and/or cohesion.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
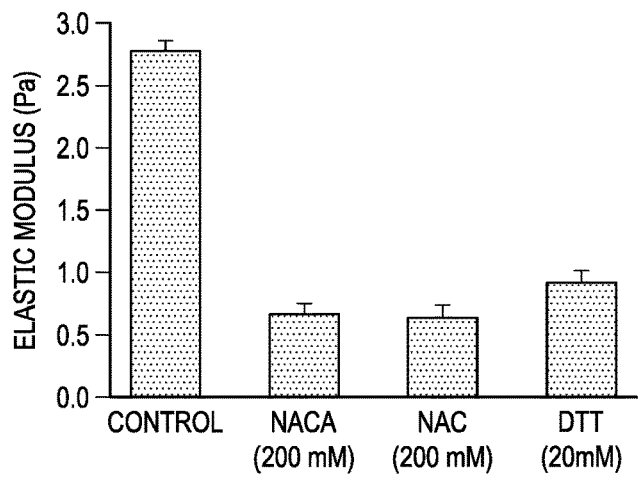
FIGS. 1A and 1B show the results of three experimental replicates from the rheology study comparing NACA vs. NAC and DTT.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

N-acetyl-L-cysteine amide (NACA), also known as (R)-2-(acetylamino)-3-mercapto-propanamide, N-acetyl-L-cysteinamide, or acetylcysteinamide, has the structure:

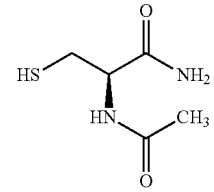

N-acetylcysteine amide (NACA), the amide form of N-acetyl-L-cysteine (NAC), acts as a carrier of NAC.

(2R,2R')-3,3'-disulfanediyl bis(2-acetamidopropanamide) (diNACA), has the structure:

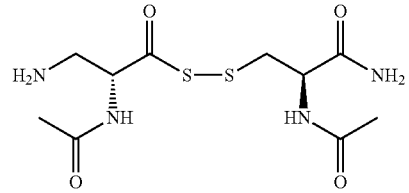 [SMILES: CC(=O)N[C@@H](CSSC(=O)[C@@H](CN)NC(C)=O)C(N)=O]

(2R,2R')-3,3'-disulfanediyl bis(2-acetamidopropanamide) (diNACA), the dimer form of N-acetyl-L-cysteine amide, acts as a carrier of NAC or cysteine.

Gluthathione (GSH) is a tripeptide, c-L-glutamyl-L-cysteinyl-glycine, found in all mammalian tissues. It has several important functions including detoxification of electrophiles, scavenging ROS<maintaining the thiol status of proteins, and regeneration of the reduced forms of vitamins C and E. GSH is the dominant non-protein thiol in mammalian cells; as such it is essential in maintaining the intracellular redox balance and the essential thiol status of proteins. Also, it is necessary for the function of some antioxidant enzymes such as the glutathione peroxidases.

Intracellular GSH levels are determined by the balance between production and loss. Production results from de novo synthesis and regeneration of GSH from GSSG by GSSG reductase. Generally there is sufficient capacity in the GSSG reductase system to maintain all intracellular GSH in the reduced state, so little can be gained by ramping up that pathway. The major source of loss of intracellular GSH is transport out of cells. Intracellular GSH levels range from 1-8 mM while extracellular levels are only a few µM; this large concentration gradient essentially precludes transport of GSH into cells and once it is transported out of cells, it is rapidly degraded by γ-glutamyltranspeptidase. Inhibition of GSH transporters could theoretically increase intracellular GSH levels, but is potentially problematic because the transporters are not specific for GSH and their suppression could lead imbalance of other amino acids and peptides. Thus, intracellular GSH levels are modulated primarily by changes in synthesis.

GSH is synthesized in the cytosol of virtually all cells by two ATP-requiring enzymatic steps: L-glutamate+L-cysteine+ATP [→] γ-glutamyl-L-cysteine+ADP+Pi and γ-glutamyl-L-cysteine+L-glycine+ATP [→] GSH+ADP+Pi. The first reaction is rate-limiting and is catalyzed by glutamate cysteine ligase (GCL, EC 6.3.2.2). GCL is composed of a 73 Kd heavy catalytic subunit (GCLC) and a 30 Kd modifier subunit (GCLM), which are encoded by different genes. GCCL is regulated by nonallosteric competitive inhibition of GSH (Ki=2.3 mM) and by the availability of L-cysteine. The apparent $K_m$ of GLC for glutamate is 1.8 mM and intracellular glutamate concentration is roughly 10-fold higher so that glutamate is not limiting, but the Km for cysteine is 0.1-0.3 mM, which approximates its intracellular concentration. The second reaction is catalyzed by GSH synthase (GS, EC 6.3.2.3), which is 118 Kd and composed of two identical subunits. While GS is not felt to be important in regulation of GSH synthesis under normal conditions, it may play a role under stressful conditions because in response to surgical trauma, GSH levels and GS activity were reduced while GCL activity was unchanged. Furthermore, compared to increased expression of GCLC alone, increased expression of both GCLC and GS resulted in higher levels of GSH. In order to maximize the effects of increasing synthetic enzymes, it is necessary to provide increased levels of cysteine. In cultured neurons, 90% of cysteine uptake occurs through by the sodium-dependent excitatory amino acid transporter (EAAT) system. There are five EAATs and cysteine uptake by neurons occurs predominantly by EAAT3 more commonly known as excitatory amino acid carrier-1 (EAAC1). Under normal circumstances most EAAC1 is in the ER and only translocates to the plasma membrane when activated. This translocation is negatively regulated by glutamate transporter associated protein 3-18 (GTRAP3-18) and suppression of GTRAP3-18) increased GSH levels in neurons. Thus, internalization of cysteine provides a road block for GSH synthesis, but fortunately it can be bypassed by N-acetylcysteine (NAC) which readily enters cells even in the absence of activated EAAC1. Systemically administered NAC gains access to the CNS, increases GSH levels, and provides benefit in neurodegenerative disorders in which oxidative stress is an important part of the pathogenesis.

All cellular compartments must be protected against oxidative damage, including the cytoplasm, mitochondria and the nucleus. The present inventors have previously performed gene transfer of enzymes that detoxify reactive oxygen species, but that approach requires expression of two enzymes in the cytoplasm and two enzymes in mitochondria. In contrast, the present invention provides for protection of all cellular compartments with expression of only two enzymes in the cytosol because GSH is able to diffuse everywhere throughout cells.

NAC is used for the treatment of acetaminophen overdose at a dose of 140 mg/kg as the loading dose, followed by 70 mg/kg every 4 hours for 17 doses, starting 4 hours after the loading dose. In clinical studies, NAC has been administered orally from 400 to 1000 mg once daily and from 200 to 600 mg three times daily. However, following an oral dose of 600 mg in humans, NAC is rapidly absorbed and then rapidly cleared. The plasma half-life of NAC has been reported to be 2.5 hours and no NAC is detectable 10-12 hours after administration. During absorption, NAC is rapidly metabolized to cysteine, which is a direct precursor of glutathione. In accordance with an embodiment, the present invention provides a method for the prevention, amelioration, or treatment of a disease or condition associated with oxidative stress in a subject comprising administration of a therapeutically effective amount of NACA, to increase the amount of glutathione expressed in the tissues of the subject.

As used herein, "active oxygen species" or "reactive oxygen species" are understood as transfer of one or two electrons produces superoxide, an anion with the form $O_2"$, or peroxide anions, having the formula $O_2\_"$ or compounds containing an O—O single bond, for example hydrogen peroxides and lipid peroxides. Such superoxides and peroxides are highly reactive and can cause damage to cellular components including proteins, nucleic acids, and lipids.

As used herein, the term "agent" refers to a therapeutically active compounds or a potentially therapeutic active compound, e.g., an antioxidant. An agent can be a previously known or unknown compound. As used herein, an agent is typically a non-cell based compound, however, an agent can include a biological therapeutic agent, e.g., peptide or nucleic acid therapeutic, e.g., siRNA, shRNA, cytokine, antibody, etc.

Oxidation is a chemical reaction that transfers electrons from a substance to an oxidizing agent. Such reactions can be promoted by or produce superoxide anions or peroxides. Oxidation reactions can produce free radicals, which start chain reaction that damage cells. Antioxidants terminate these chain reactions by removing free radical intermediates, and inhibit other oxidation reactions by being oxidized themselves. As a result, antioxidants are often reducing agents such as thiols, ascorbic acid or polyphenols. Antioxidants include, but are not limited to, α-tocopherol, ascorbic acid, Mn(III)tetrakis (4-benzoic acid) porphyrin, α-lipoic acid, and n-acetylcysteine.

As used herein, the terms "effective amount" or "effective doses" refer to that amount of an agent to product the intended pharmacological, therapeutic or preventive results. The pharmacologically effective amount results in the amelioration of one or more signs or symptoms of a disease or condition or the advancement of a disease or conditions, or causes the regression of the disease or condition. For example, a therapeutically effective amount preferably refers to the amount of a therapeutic agent that decreases vision loss, the loss of overall visual acuity, the loss of visual field, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject over a defined period of time, e.g., 2 weeks, one month, 2 months, 3 months, 6 months, one year, 2 years, 5 years, or longer. More than one dose may be required to provide an effective dose.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such as treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as an improvement of symptoms, a cure, a reduction in disease signs or symptoms, extension of life, improvement in quality of life, or other effect generally recognized as positive by medical doctors familiar with treating the particular type of disease or condition.

As used herein, the terms "peroxidases" or "a peroxide metabolizing enzyme" refer to a large family of enzymes that typically catalyze a reaction of the form:

$ROOR_1$+electron donor (2 e−)+2H+→ROH+$R_1$OH For many of these enzymes the optimal substrate is hydrogen peroxide, wherein each R is H, but others are more active with organic hydroperoxides such as lipid peroxides. Peroxidases can contain a heme cofactor in their active sites, or redox—active cysteine or selenocysteine residues.

As used herein, the term phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations, particularly phosphate buffered saline solutions which are preferred for intraocular delivery.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, intraocular, intravitreal, subretinal, and/or other routes of parenteral administration. The specific route of administration will depend, inter alia, on the specific cell to be targeted. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, "plurality" is understood to mean more than one. For example, a plurality refers to at least two, three, four, five, or more.

As used herein, the term a "polypeptide" or "peptide" is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full-length proteins (e.g., fully processed proteins) as well as shorter amino acids sequences (e.g., fragments of naturally occurring proteins or synthetic polypeptide fragments).

As used herein, the term "small molecule" refers to a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

As used herein, the term "subject" refers to living organisms, in particular, humans. In certain embodiments, the living organism is an animal, in certain preferred embodiments, the subject is a mammal, in certain embodiments, the subject is a domesticated mammal or a primate including a non-human primate. Examples of subject include humans, monkeys, dogs, cats, mice, rates, cows, horses, goats, and sheep. A human subject may also be referred to as a subject or patient.

As used herein, "superoxide dismutase" is understood as an enzyme that dismutation of superoxide into oxygen and hydrogen peroxide. Examples include, but are not limited to SOD1, SOD2, and SOD3. Sod1 and SOD3 are two isoforms of Cu—Zn-containing superoxide dismutase enzymes exists in mammals. Cu—Zn-SOD or SOD1, is found in the intracellular space, and extracellular SOD (ECSOD or SOD3) predominantly is found in the extracellular matrix of most tissues.

As used herein, the term "therapeutically effective amount," refers to an amount of an agent which is effective, upon single or multiple does administration to the cell or subject, in prolonging the survivability of the patient with such a disorder, reducing one or more signs or symptoms of the disorder, preventing or delaying and the like beyond that expected in the absence of such treatment.

An agent or other therapeutic intervention can be administered to a subject, either alone or in combination with one or more additional therapeutic agents or interventions, as a pharmaceutical composition in mixture with conventional excipient, e.g., pharmaceutically acceptable carrier, or therapeutic treatments.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, Pa., 1985). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

The present invention is directed to the use of NACA to prevent and/or treat radiation pneumonitis and treatment of pulmonary function in Cystic Fibrosis. In one embodiment, the present invention includes a method for use of N-acetylcysteine amide (NACA) or (2R,2R')-3,3'-disulfanediyl bis(2-acetamidopropanamide) (diNACA) for the prevention and/or treatment of radiation pneumonitis and treatment of pulmonary function in Cystic Fibrosis in a human that comprises administering to the human therapeutically effective amount of NACA. In some embodiments, the NACA is provided in or with a pharmaceutically acceptable carrier. In other embodiments, the NACA is administered intraocularly, subretinally, intravitreally, orally, intravenously, intramuscularly, topically, sublingually, or rectally.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the forgoing guidelines.

Ranges provided herein are understood to be shorthand for all of the values within the range.

As used herein, the embodiments of this invention are defined to include pharmaceutically acceptable derivatives thereof. A "pharmaceutically acceptable derivative" means any pharmaceutically salt, ester, salt of an ester, or other derivative of a compound of this invention which, upon administration to a recipient, is capable of providing (directly or indirectly) a compound of this invention. Particularly favored derivatives are those that increase the bioavailability of the compounds of this invention when such compounds are administered to a mammal (e.g., by allowing an orally administered compound to be more readily absorbed into the blood, to increase serum stability or decrease clearance rate of the compound) or which enhance delivery of the parent compound to a biological compartment (e.g., the brain or lymphatic system) relative to the parent species. Derivatives include derivatives where a group which enhances aqueous solubility or active transport through the gut membrane is appended to the structure of formulae described herein.

The embodiments of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-napthalenesulfonate, nicotinate, nitrate, palmoate, phosphate, picrate, pivalate, propionate, salicylate, succinate, sulfate, tartrate, tosylate, and undeconaoate. Salts derived from appropriate bases include alkali metal (e.g., sodium), alkaline earth metal (e.g., magnesium), ammonium and N-(alkyl)4+ salts. This invention also envisions the quaternization of any basic nitrogen-containing groups of the compounds disclosed herein. Water or oil-soluble or dispersible products may be obtained by such quaternization.

The embodiments of the invention can, for example, be administered by injection, intraocularly, intravitreally, subretinal, intravenously, intraarterially, subdermally, intramuscularly, or subcutaneously; or orally, buccally, nasally, transmucosally, directly to a diseased organ by catheter, topically, or in an ophthalmic preparation, with a dosage ranging from about 0.001 to about 100 mg/kg of body weight, or according to the requirements of the particular drug and more preferably from 0.5-10 mg/kg of body weight. It is understood that when a compound is delivered directly to the eye, considerations such as body weight have less bearing on the dose.

Frequency of dosing will depend on the agent administered, the progression of the disease or condition in the subject, and other considerations known to those of skill in the art. For example, pharmacokinetic and pharmacodynamics considerations for compositions delivered to the eye, or even compartments within the eye, are different, e.g., clearance in the subretinal space is very low. Therefore, dosing can be as infrequent as once a month, once every three months, once every six months, once a year, once every five years, or less. If systemic administration of antioxidants is to be performed in conjunction with administration of expression constructs to the subretinal space, it is expected that the dosing frequency of the antioxidant will be higher than the expression construct, e.g., one or more times daily, one or more times weekly.

Dosing may be determined in conjunction with monitoring of one or more signs or symptoms of the disease, e.g., visual acuity, visual field, night visions, etc. The amount of active ingredient that may be combined with the carrier materials to produce a single dosage form will vary depending upon the host treated and the particular mode of administration. A typical preparation will contain from about 1% to about 95% active compound (w/w). Alternatively, such preparations contain from about 20% to about 80% active compound. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity ad course of the disease, condition or symptoms, the patient's disposition to the disease, condition or symptoms and the judgment of the treating physician.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, TWEEN® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as TWEENs® or SPAN® and/or other similar emulsifying agents or bioavailability enhancers which are commonly used in the manufacture of pharmaceutically acceptable solid, liquid, or other dosage forms may also be used for the purposes of formulation.

In one or more embodiments, NACA or diNACA is administered in daily doses of about 0.5 to 150 mg/Kg. In other embodiments, NACA or diNACA is administered two or three times daily. In another aspect, NACA or diNACA is administered with a second active agent selected from ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

In some embodiments, the dose of NACA or diNACA for administration is, 100, 150, 150, 300, 333, 400, 500, 600, 700, 750, 800, 900, 1,000, 2,500, 5,000, 7,500, or 10,000 mg per dose. In another aspect, the dose for administration is 0.1-0.25, 0.1-0.4, 0.35-0.5, 0.5-1, 102, 1-3, 1-4, 1-5, 1-2.5, 2.5-3.5, 4-6, 5-8, 6-9, 7-10 grams per dose. In another aspect, the NACA or diNACA is delivered orally via a mini-tablet, capsule, tablet, effervescent, dual release, mixed release, sachet, powder, or liquid. In another aspect, the NACA is administered prophylactically to prevent and/or treat radiation pneumonitis and treatment of pulmonary function in Cystic Fibrosis.

In another embodiment, the present invention includes a method for preventing and/or treating radiation pneumonitis and treatment of pulmonary function in Cystic Fibrosis comprising: identifying a human in need of treatment for radiation pneumonitis and treatment of pulmonary function in Cystic Fibrosis; and administering to the human a therapeutically effective amount of NACA or diNACA sufficient to treat prevent and/or treat radiation pneumonitis and treatment of pulmonary function in Cystic Fibrosis. It will be understood that, as with the other embodiments defined above, NACA or diNACA is administered in daily doses of about 0.5 to 150 mg/Kg. In another aspect, NACA or diNACA is administered two or three times daily. In another aspect, NACA is administered with a second active agent as disclosed above.

In another aspect, the dose of NACA or diNACA for administration is 100, 150, 150, 300, 333, 400, 500, 600, 700, 750, 800, 900, 1,000, 2,500, 5,000, 7,500, or 10,000 mg per dose. In another aspect, the dose for administration is 0.1-0.25, 0.1-0.4, 0.35-0.5, 0.5-1, 102, 1-3, 1-4, 1-5, 1-2.5, 2.5-3.5, 4-6, 5-8, 6-9, 7-10 grams per dose. In another aspect, the NACA or diNACA is delivered orally via a mini-tablet, capsule, tablet, effervescent, dual release, mixed release, sachet, powder, or liquid. In another aspect, NACA or diNACA is administered prophylactically to prevent and/or treat radiation pneumonitis and treatment of pulmonary function in Cystic Fibrosis.

As used herein, "susceptible to" or "prone to" or "predisposed to" a specific disease or condition or the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200% or more.

Mucolysis.

In pulmonary medicine, there has been a long-standing need to treat diseases associated with mucus accumulation in the lungs. The overarching goal of an inhaled therapy is to clear the hyperconcentrated, adherent mucus that causes airflow obstruction, inflammation, and infection. Reducing the molecular mass of mucin gel polymers is a straightforward approach to treat a broad spectrum of muco-obstructive diseases and was tested several decades ago with NAC. Studies from the 1960s suggest that high concentrations of NAC could remove mucus plugs in subjects with CF or tracheostomies when delivered topically via bronchoscopy (25-28) (Webb W R. New mucolytic agents for sputum liquefaction. Postgrad Med 1964; 36:449-453; Matthews L W, Doershuk C F. Inhalation therapy and postural drainage for the treatment of cystic fibrosis. Bibl Paediatr 1967; 86:297-314; Miller W F. Aerosol therapy in acute and chronic respiratory disease. Arch Intern Med 1973; 131:148-155; Dietzsch H J, Gottschalk B, Heyne K, Leupoid W, Wunderlich P. Cystic fibrosis: comparison of two mucolytic drugs for inhalation treatment (acetylcysteine and arginine hydrochloride). Pediatrics 1975; 55:96-100). Studies from the early 1970s described modest improvements in lung function following inhalation NAC treatment, which may have reflected the osmotic activity of the high NAC concentrations (20%, 1,200 mOsm) aerosolized. Indeed, human studies (Clarke S W, Thomson M L, Pavia D. Effect of mucolytic and expectorant drugs on tracheobronchial clearance in chronic bronchitis. Eur J Respir Dis Suppl 1980; 110:179-191; Pavia D, Sutton P P, Lopez-Vidriero M T, Agnew J E, Clarke S W. Drug effects on mucociliary function. Eur J Respir Dis Suppl 1983; 128: 304-317) showed that the effects of NAC on mucociliary clearance were mimicked by equiosmotic concentrations of NaCl. Studies in WT mice paralleled these findings, demonstrating that delivery of high concentrations of NAC induced epithelial cell damage and acute neutrophilic responses that may in part have reflected the large osmotic load deposited. The limited efficacy of NAC, coupled with the off-target irritation effects, including cough and bronchospasm, appear responsible for its failure in clinical pulmonary medicine as an inhaled mucolytic (6-9) (Tam J, Nash E F, Ratjen F, Tullis E, Stephenson A. Nebulized and oral thiol derivatives for pulmonary disease in cystic fibrosis. Cochrane Database Syst Rev 2013; (7):CD007168; Nash E F, Stephenson A, Ratjen F, Tullis E. Nebulized and oral thiol derivatives for pulmonary disease in cystic fibrosis. Cochrane Database Syst Rev 2009; (1):CD007168; Rogers D F. Mucoactive drugs for asthma and COPD: any place in therapy? Expert Opin Investig Drugs 2002; 11:15-35; Poole P, Chong J, Cates C J. Mucolytic agents versus placebo for chronic bronchitis or chronic obstructive pulmonary disease. Cochrane Database Syst Rev 2015; (7):CD001287). (Ehre et al. An Improved Inhaled Mucolytic to Treat Airway Muco-obstructive Diseases. Am J Respir Crit Care Med. 2019 Jan. 15; 199(2):171-180. doi: 10.1164/rccm.201802-0245OC).

Inhaled mucolytic agents are designed to decrease the viscoelasticity of airway secretions, improve mucociliary clearance, and reduce the mucus burden in the lungs of patients suffering from muco-obstructive pulmonary diseases. Reducing agents break the disulfide bonds that connect mucin macromolecules by donating electrons to the thiol groups of mucin monomer cysteine residues, changing the rheology of mucin-rich secretions.

Studies were conducted to elucidate the mechanisms for the clinical failure of NAC and test whether a novel molecule in the thiol-reducing class could overcome these deficiencies. (Ehre et al. An Improved Inhaled Mucolytic to Treat Airway Muco-obstructive Diseases. Am J Respir Crit Care Med. 2019 Jan. 15; 199(2):171-180. doi: 10.1164/rccm.201802-0245OC) Small-molecule reducing agents reduce protein disulfide bonds via a stoichiometric bimolecular chemical reaction. The speed of the reaction is directly dependent on their intrinsic activity and access to the target S—S bonds. The efficacy of reduction is also dependent on the residence time on airway surfaces of a given agent. NAC has a low intrinsic reducing activity. This deficiency is compounded by the alkaline pKa of its thiol group. The thiolate anion (S—) form of the NAC sulfur is required for attack on mucin S—S bonds. On a normal airway surface with a pH of 7.0-7.2, NAC is then 99% in the inactive protonated form. Although NAC will cycle from SH (inactive) to S-(active) forms over time in airway mucus, this process is slow and requires NAC to be retained on the airway surfaces for long time periods to react to completion. However, NAC is rapidly cleared and/or absorbed from epithelial surfaces and, consequently, not present at sufficient concentrations or durations to be efficacious in human airways. Consistent with these analyses, NAC administered at maximum tolerated doses (20%) did not produce mucus reduction in CF subjects. (Ehre et al. An Improved Inhaled Mucolytic to Treat Airway Muco-obstructive Diseases. Am J Respir Crit Care Med. 2019 Jan. 15; 199(2):171-180. doi: 10.1164/rccm.201802-0245OC)

Surprisingly, diNACA, did exhibit mucolytic activity. This is surprising since it was hypothesized that the secondary —S—S— bond would not be active in situ.

Example 1: NACA, diNACA and DTT Effects on Human Bronchial Epithelial (HBE) Airway Mucus Mucus obstruction in the airway is a pathway of considerable interest, given that this is one of the primary areas that can cause the lung to fail. It is well established that highly concentered mucus associated with diseases such as CF and COPD is not effectively or efficiently cleared by the human lung, leading to a host of respiratory complications. One potential method of restoring optimal mucus clearance is to use a powerful mucolytic agent to effectively breakdown the mucus into more easily cleared particle sizes.

In the Example 1, the inventors assessed the ability of NACA to reduce the rheological properties of a concentrated (cystic fibrosis-like) mucus, making it more flowable. In this phase, NACA was compared to both a classical clinical reducing agent (N-acetylcysteine; NAC) as well as a potent laboratory reducing agent (Dithiothreitol; DTT). The studies in this phase of the project were performed at a single dose, 200 mM for the mono-thiols NACA and NAC and 20 mM for the di-thiol DTT.

Methods. In this study, a single preparation of human bronchial epithelial (HBE) airway mucus at 5.4% solids (i.e., wet-to-dry ratio) was utilized as the test mucus sample. This sample was thawed on ice and split into 4 separate groups. The appropriate amount of test agent (see above) was added to each mucus sample: (1) PBS (vehicle control), (2) NACA, (3) NAC, and (4) DTT. Samples were incubated for 60 minutes at 37ÀöC prior to analysis. Note, the final mucus concentration of each sample (after test agent addition) was ~4.9% solids.

The viscoelastic (i.e., rheological) properties of each mucus preparation was made using a cone-and-plate rheometer (DH3; TA Instruments). For each study, 100 Œ°l of sample was loaded onto the rheometer. Stress controlled sweeps (for viscous and elastic modulus determination) were performed over frequencies from 10-2-102 Hz. To assess yield stress, creep-recovery studies were performed at stresses from 0.05 to 1.5 Pa. Next, the cohesive stress of each sample (i.e., how much force it takes to tear the mucus) was obtained using a peel tester (see Button et. al, PNAS 2018). Studies here were performed at a peel rate of 1 mm/sec.

Figure 1B:
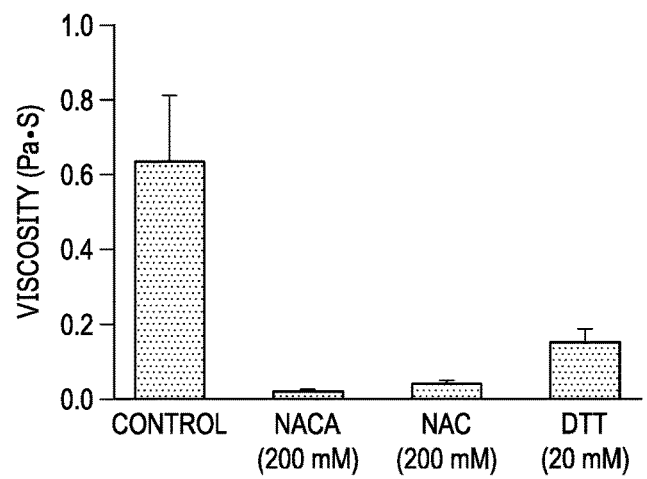
Figure 1C:
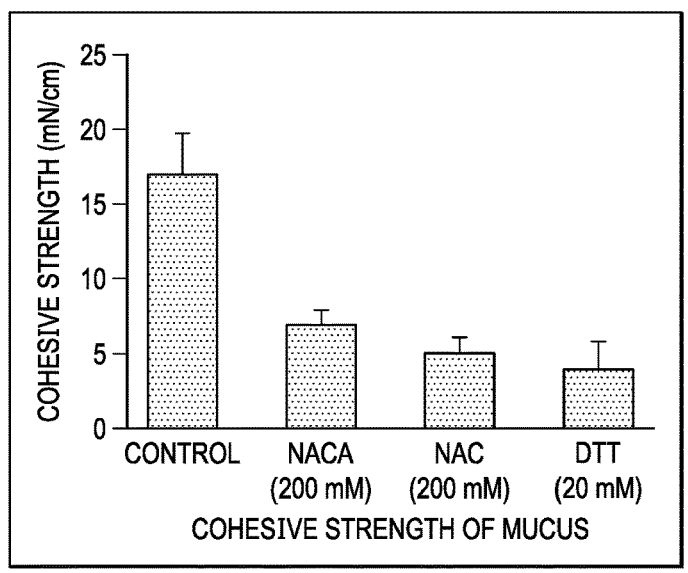
FIG. 1C shows the cohesive strength of mucus.

Data in FIGS. 1A to 1C show the results of three experimental replicates from the rheology study comparing NACA vs. NAC and DTT. For all agents tested, there was a significant reduction in both the elasticity and viscosity of the concentrated mucus sample (versus control; all p<0.01). For both elasticity and viscosity, NACA and NAC were significantly less than the DTT group (all p<0.05). At the 200 mM dose, these was no significant difference between NACA and NAC.

Note that studies investigating the yield stress of mucus were inconclusive. At the 200 mM dose for NACA and NAC, the mucus "flowed" at the lowest stress used in this study (0.05 Pa). For comparison, the control sample required significantly higher stresses (1.3 Pa) to yield. While an important positive finding, the actual yield stress value for each test agent could not be obtained.

Cohesive Strength.

The cohesive strength of mucus is a measure of the force required to "tear" mucus apart. Such tearing is important for high-speed airflow removal of mucus from airway surfaces during cough. In many lung diseases, such as CF, mucus is harder to cough out of the airway. As such, reducing the cohesive strength of mucus is predicted to improve the cough clearability of mucus in disease. FIG. 1C shows the results of the cohesive strength of mucus before and after the addition of each test agent. In this study all three agents significantly reduced the cohesive strength of mucus. While DTT was slightly better than NAC and NACA, there was no significant difference between each of the three test agents.

At the 200 mM dose, NACA was very effective at reducing the viscoelasticity and cohesive strength of mucus. The result is a transformation from a very "gel-like" mucus to one that flows, making it easier to clear from the lungs. While there was no observed difference between NACA and NAC at this dose, the values obtained from each test article were on par (or better) than the very potent reducing agent, DTT, which can fully reduce mucins at 20 mM.

Example 2: Effects of NACA, diNACA and DTT on Human CF Sputum

Human CF sputum was collected. Reducing agents such as NACA, diNACA and DTT should reduce the viscosity of sputum. Elastic modulus was assessed for NACA, diNACA, compared to positive control, DTT. The concentration of human CF sputum was 3.5% in all samples. Sample preparation:

20 mM diNACA was prepared directly by adding powder to sputum 20 mM DTT and 200 mM NACA were prepared by spiking sputum with solutions of each reducing agent in saline. Elastic modulus and creep recovery (yield stress (viscosity)) was measured using a rheometer.

Figure 2A:
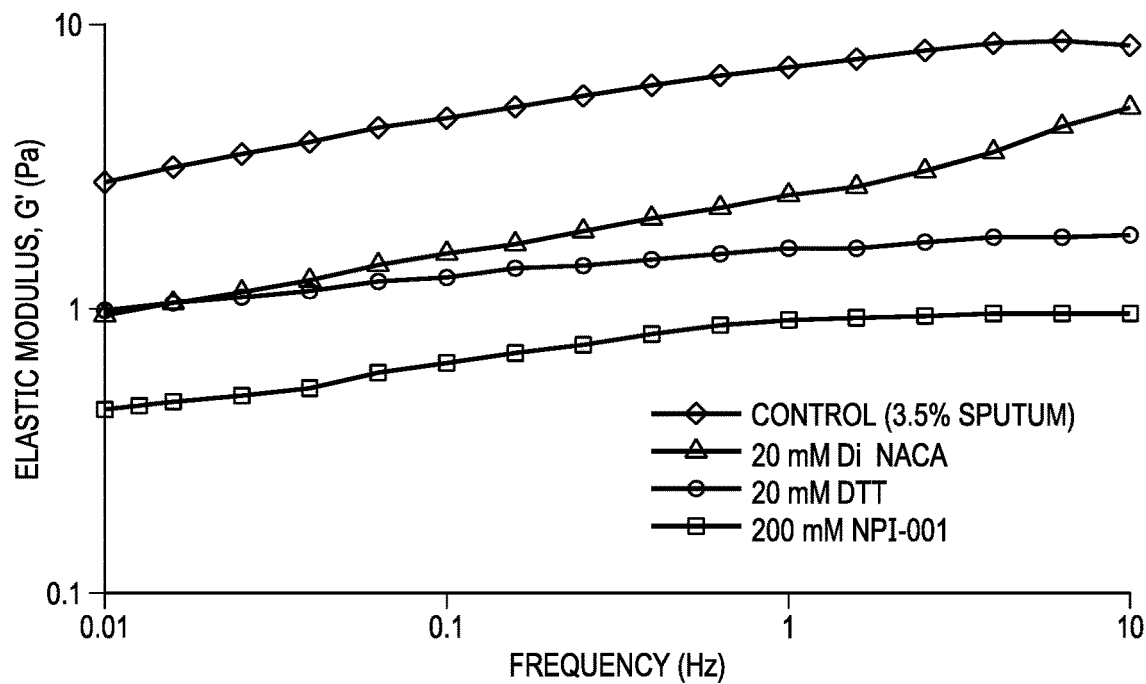
FIG. 2A shows a frequency sweep of NACA, diNACA and DTT in human CF sputum.
Figure 2B:
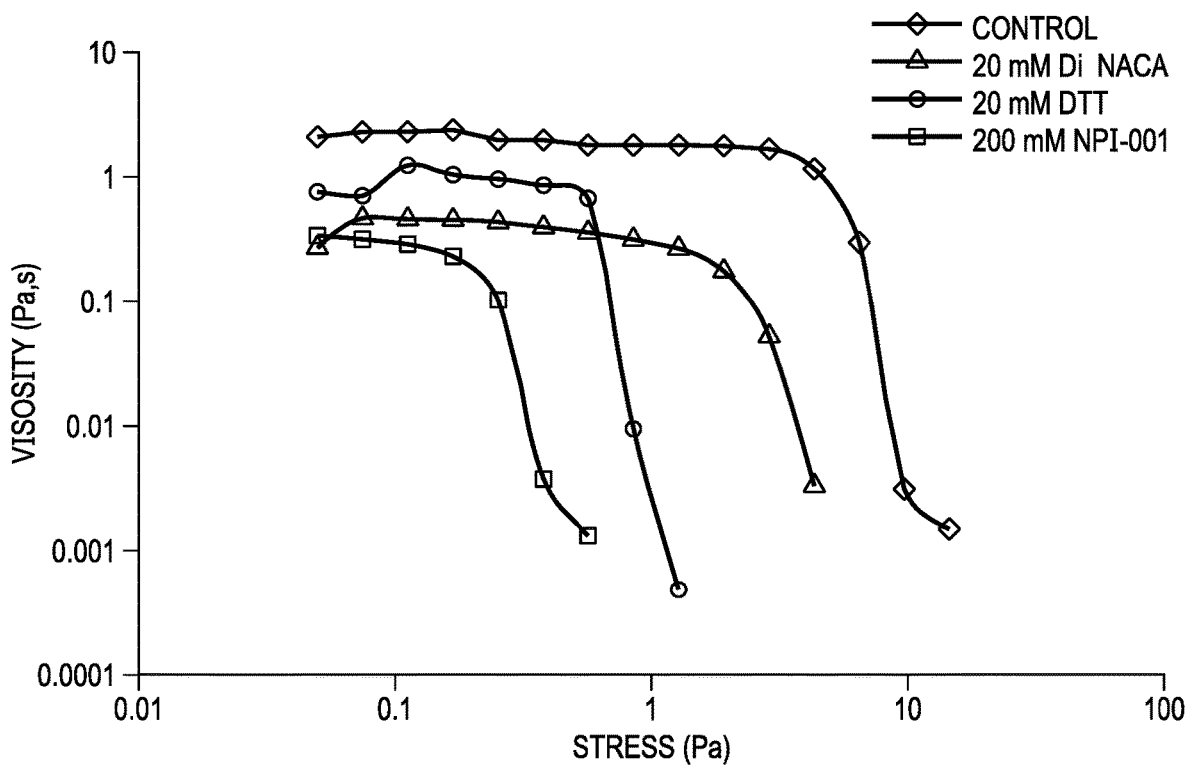
FIG. 2B shows the creep recovery or yield stress (viscosity) of human CF sputum after pretreatment with NACA, diNACA or DTT.

FIG. 2A shows a frequency sweep of NACA, diNACA and DTT in human CF sputum, and FIG. 2B shows the creep recovery or yield stress (viscosity) of human CF sputum after pretreatment with NACA, diNACA or DTT.

Figure 3:
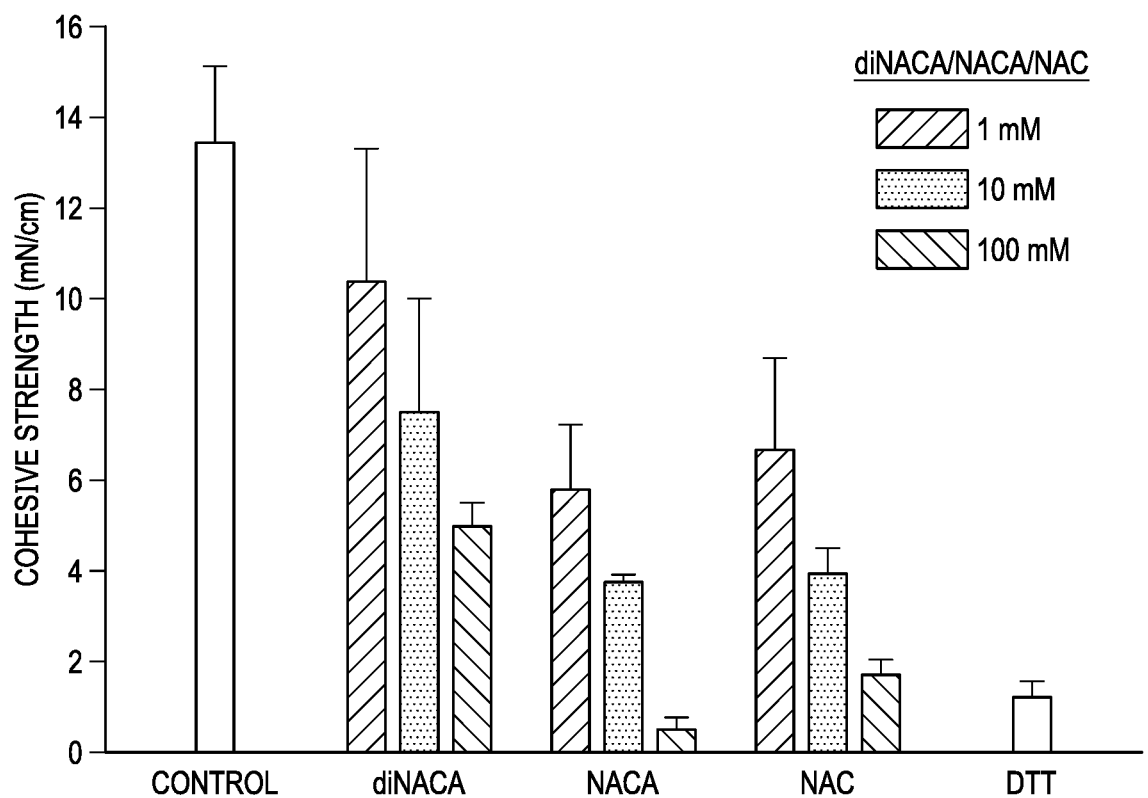
FIG. 3 is a graph that shows cohesion of NACA, diNACA and DTT in human CF sputum.
Figure 4:
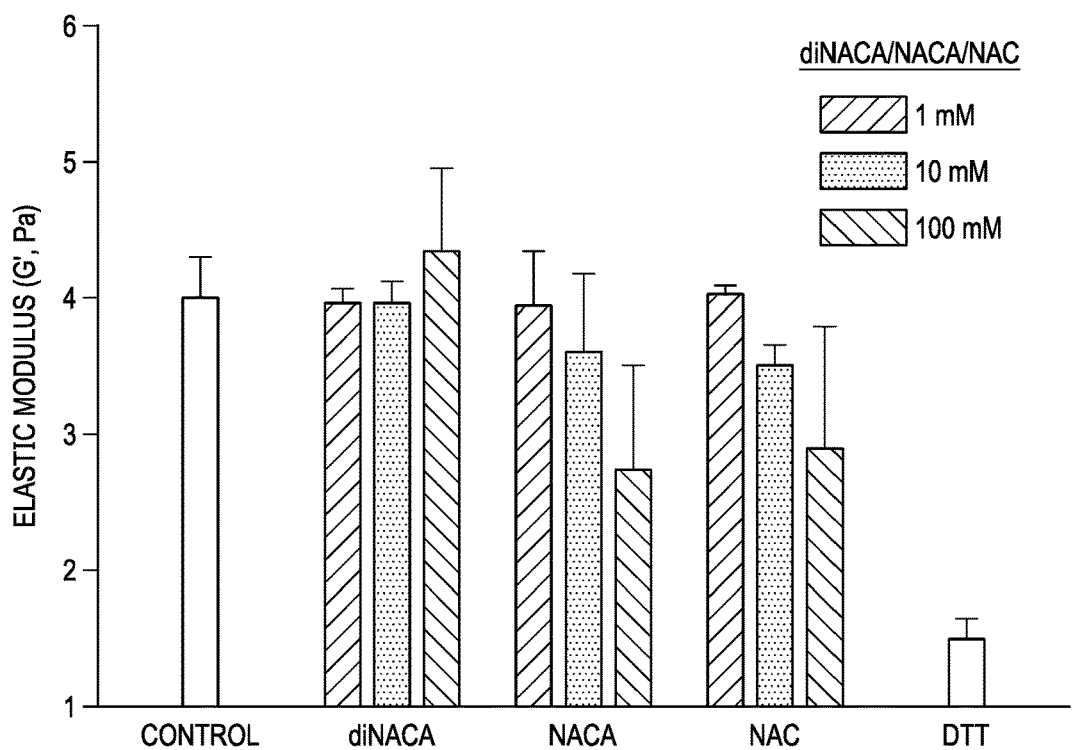
FIG. 4 is a graph that shows cohesion of NACA, diNACA and DTT in human CF sputum.
Figure 5:
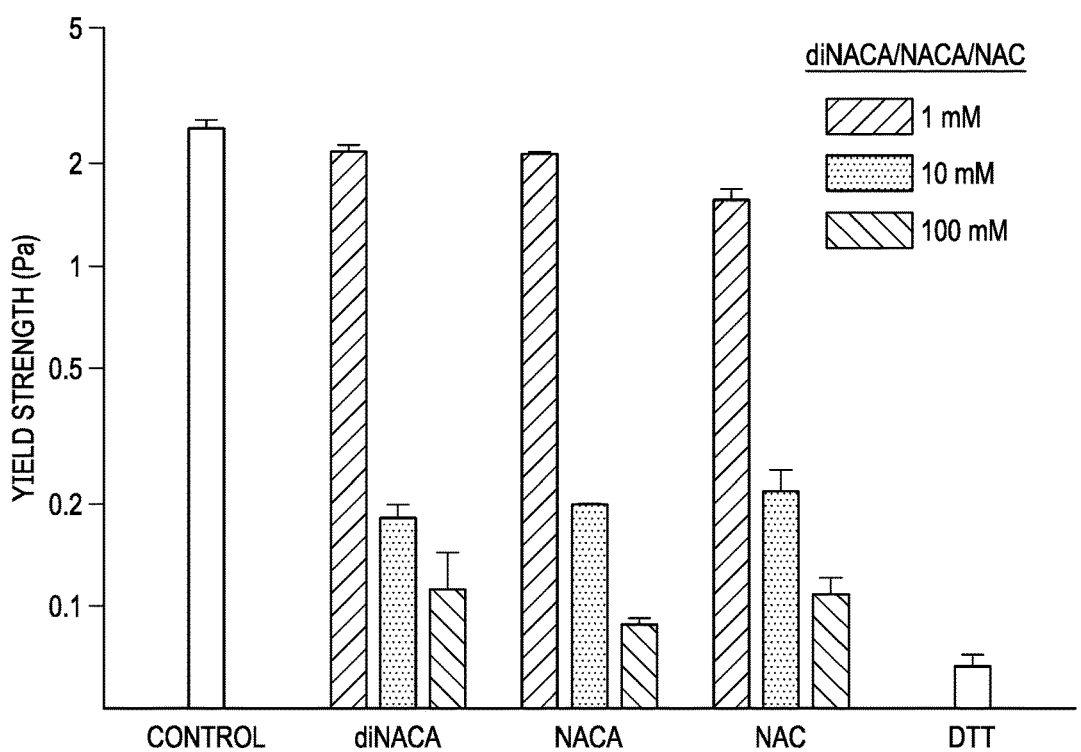
FIG. 5 is a graph that shows yield strength of NACA, diNACA and DTT in human CF sputum.

FIG. 3 is a graph that shows cohesion of NACA, diNACA and DTT in human CF sputum. FIG. 4 is a graph that shows cohesion of NACA, diNACA and DTT in human CF sputum. FIG. 5 is a graph that shows yield strength of NACA, diNACA and DTT in human CF sputum.

In accordance with an embodiment, the present invention provides a method for the use of N-acetylcysteine amide (NACA) or (2R,2R')-3,3'-disulfanediyl bis(2-acetamidopropanamide) (diNACA) for prevention and treatment of radiation pneumonitis and treatment of pulmonary function in Cystic Fibrosis (CF), chronic obstructive pulmonary disease (COPD), bronchitis, or respiratory disorder due to oxidative stress, in an animal or human comprising, consisting essentially of, or consisting of: administering to the animal or human a therapeutically effective amount of NACA or diNACA. In one aspect, NACA or diNACA is provided in or with a pharmaceutically acceptable carrier. In another aspect, the NACA or diNACA is administered intraocularly, subretinally, intravitreally, orally, intravenously, intramuscularly, topically, sublingually, by inhalation, or rectally. In another aspect, the NACA or diNACA is administered in daily doses of about 0.5 to 150 mg/Kg. In another aspect, NACA is administered two or three times daily. In another aspect, NACA or diNACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytouene (BHT), lecithin, propyl gallate, α-tocopherol, citric acid, ethylenediamine tetraacetic acid (EDTA), sorbitol, tartaric acid, or phosphoric acid. In another aspect, the dose for administration is 100, 150, 150, 300, 333, 400, 500, 600, 700, 750, 800, 900, 1,000, 2,500, 5,000, 7,500, or 10,000 mg per dose. In another aspect, the does for administration is 0.1-0.25, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, the NACA or diNACA is delivered orally via a mini-tablet, capsule, tablet, effervescent, dual release, mixed release, sachet, powder, aerosol, spray or liquid. In another aspect, the NACA or diNACA is administered prophylactically to prevent age-related macular degeneration. In another aspect, the animal is a human. In another aspect, the diNACA reduces mucus viscosity, elasticity and/or cohesion.

In accordance with another embodiment, the present invention includes a method for the treatment of radiation pneumonitis and treatment of pulmonary function in Cystic Fibrosis (CF), chronic obstructive pulmonary disease (COPD), bronchitis or respiratory disorder due to oxidative stress, or reduction of mucus viscosity and/or elasticity comprising, consisting essentially of, or consisting of: identifying a human in need of treatment for radiation pneumonitis and treatment of pulmonary function in Cystic Fibrosis (CF), chronic obstructive pulmonary disease (COPD), bronchitis or respiratory disorder due to oxidative stress, or reduction of mucus viscosity and/or elasticity; and administering to the human a therapeutically effective amount of NACA or diNACA sufficient to treat radiation pneumonitis and treatment of pulmonary function in Cystic Fibrosis (CF), chronic obstructive pulmonary disease (COPD), or bronchitis. In one aspect, the NACA or diNACA is provided in or with a pharmaceutically acceptable carrier. In another aspect, the NACA or diNACA is administered intraocularly, subretinally, intravitreally, orally, intravenously, intramuscularly, topically, sublingually, by inhalation, or rectally. In another aspect, the NACA or diNACA is administered in daily doses of about 0.5 to 150 mg/Kg. In another aspect, NACA or diNACA is administered two or three times daily. In another aspect, NACA or diNACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytouene (BHT), lecithin, propyl gallate, α-tocopherol, citric acid, ethylenediamine tetraacetic acid (EDTA), sorbitol, tartaric acid, or phosphoric acid. In another aspect, the dose for administration is 100, 150, 150, 300, 333, 400, 500, 600, 700, 750, 800, 900, 1,000, 2,500, 5,000, 7,500, or 10,000 mg per dose. In another aspect, the does for administration is 0.1-0.25, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, the NACA or diNACA is delivered orally via a mini-tablet, capsule, tablet, effervescent, dual release, mixed release, sachet, powder, aerosol, spray or liquid. In another aspect, the NACA or diNACA is administered prophylactically to treat and/or prevent radiation pneumonitis and treatment of pulmonary function in Cystic Fibrosis (CF), chronic obstructive pulmonary disease (COPD), or bronchitis, or respiratory disorder due to oxidative stress, and diNACA as a mucolytic agent. In another aspect, the diNACA reduces mucus viscosity, elasticity and/or cohesion.

A method for prevention or treatment of radiation pneumonitis and treatment of pulmonary function in Cystic Fibrosis (CF), chronic obstructive pulmonary disease (COPD), or bronchitis in a human subject that comprises, consists essentially of, or consists of: administering to the human patient a therapeutically effective amount of NACA or diNACA sufficient to treat or prevent radiation pneumonitis and treatment of pulmonary function in Cystic Fibrosis (CF), chronic obstructive pulmonary disease (COPD), or bronchitis. In another aspect, the diNACA reduces mucus viscosity, elasticity and/or cohesion.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" issued to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refer condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organization cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for treating Cystic Fibrosis (CF), or bronchitis, in a subject that comprises:
   identifying a patient in need of for treatment of Cystic Fibrosis (CF), or bronchitis, by reduction of mucus viscosity and/or elasticity; and
   administering to the patient a therapeutically effective amount of N-acetyl cystine amine (NACA) or (2R, 2R')-3,3'-disulfanediyl bis(2-acetamidopropanamide (diNACA).

2. The method of claim 1, wherein the NACA or diNACA is provided in or with a pharmaceutically acceptable carrier.

3. The method of claim 1, wherein the NACA or diNACA is administered orally, intravenously, intramuscularly, enterally, intraocularly, subretinally, intravitreally, topically, ocularly, sublingually, by inhalation or rectally.

4. The method of claim 1, wherein the NACA or diNACA is administered in daily doses of about 0.5 to 150 mg/Kg.

5. The method of claim 1, wherein the NACA or diNACA is administered two or three times daily.

6. The method of claim 1, wherein the NACA or diNACA is administered with a second active agent.

7. The method of claim 1, wherein the NACA or diNACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytoluene (BHT), lecithin, propyl gallate, α-tocopherol, citric acid, ethylenediamine tetraacetic acid (EDTA), sorbitol, tartaric acid, or phosphoric acid.

8. The method of claim 1, wherein the dose for administration is 100, 150, 300, 333, 400, 500, 600, 700, 750, 800, 900, 1,000, 2,500, 5,000, 7,500, or 10,000 mg per dose.

9. The method of claim 1, wherein the NACA or diNACA is delivered orally via a mini-tablet, capsule, tablet, effervescent, dual release, mixed release, sachet, powder, aerosol, spray, or liquid.

10. The method of claim 1, wherein the NACA or diNACA is administered prophylactically for prevention and treatment of Cystic Fibrosis (CF), chronic obstructive pulmonary disease (COPD), or bronchitis, or respiratory disorder due to oxidative stress.

11. The method of claim 1, wherein the therapeutically effective amount decreases at least one of the loss of night vision, the loss of overall visual acuity, the loss of visual field, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject over a defined period of time, selected from at least one of 2 weeks, one month, 2 months, 3 months, 6 months, one year, 2 years, or 5 years.

12. The method of claim 1, wherein the NACA or diNACA is delivered orally via a mini-tablet, capsule, tablet, effervescent, dual release, mixed release, sachet, powder, or liquid.

13. The method of claim 1, wherein the therapeutically effective amount decreases the loss of overall visual acuity, the loss of visual field, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject over a defined period of time, selected from at least one of 2 weeks, one month, 2 months, 3 months, 6 months, one year, 2 years, or 5 years.

14. The methods of claim 1, wherein diNACA reduces at least one of: mucus viscosity, elasticity, or cohesion.

15. A method for treatment of chronic obstructive pulmonary disease (COPD), or bronchitis comprising:
    administering to the human patient a therapeutically effective amount of diNACA sufficient to treat, chronic obstructive pulmonary disease (COPD), or bronchitis.

* * * * *